US00PP33959P2

(12) United States Plant Patent
Meilland

(10) Patent No.: US PP33,959 P2
(45) Date of Patent: Feb. 22, 2022

(54) MINIATURE ROSE PLANT NAMED 'MEIYEJOI'

(50) Latin Name: *Rosa hybrida*
Varietal Denomination: MEIYEJOI

(71) Applicant: THE CONARD PYLE COMPANY, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/384,957

(22) Filed: Jul. 26, 2021

(51) Int. Cl.
*A01H 5/02* (2018.01)
*A01H 6/74* (2018.01)

(52) U.S. Cl.
USPC ..... Plt./116

(58) Field of Classification Search
USPC ..... Plt./101, 116
See application file for complete search history.

(56) References Cited

U.S. PATENT DOCUMENTS

PP16,202 P2 1/2006 Radler

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'MEIYEJOI', is disclosed. The new variety forms attractive, flat cup shaped, pink colored flowers. Attractive, dark green, dense and semi-glossy foliage is formed, which contrasts beautifully with the blossoms. A bushy growth habit is displayed. The new variety is well suited for providing attractive ornamentation in the landscape.

1 Drawing Sheet

Botanical/commercial classification:
Latin name: *Rosa hybrida.*
Varietal denomination: 'MEIYEJOI'.

SUMMARY OF THE INVENTION

The new variety of *Rosa hybrida* plant was created by artificial pollination in Le Cannet des Maures, Var, France, wherein two parents were crossed which previously had been studied in the hope that they would contribute the desired characteristics. The female parent (i.e., the seed parent) (not patented) was the product of a cross between the 'MEIPAONIA' variety (not patented) and an unnamed seedling variety. The male parent (i.e., the pollen parent) was the 'RADTKO' variety (U.S. Plant Pat. No. 16,202).

The parentage of the new variety can be summarized as follows:

('MEIPAONIA' X Unnamed Seedling) X
'RADTKO'

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) is a very floriferous miniature variety,
(b) forms a pink colored flower, and
(c) exhibits a dark green, semi-glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the ('MEIPAONIA' X Unnamed Seedling) variety (i.e., the seed parent) displays larger flowers with more petals compared to the new variety. The 'RADTKO' variety (i.e., the pollen parent) displays ochre margined with pink colored flowers, whereas the new variety displays pink colored flowers. The 'MEIPAONIA' variety (i.e., a parent of the seed parent) exhibits ocher colored blossoms, whereas the new variety exhibits pink colored blossoms. Moreover, the new variety can be readily distinguished from other similar non-parental varieties. For example, the 'MEIFOVETT' variety (not patented) displays lavender pink colored flowers compared to pink colored flowers of new variety.

The new variety has been found to undergo asexual propagation in Le Cannet des Maures, Var, France by a number of routes, including softwood cuttings, hardwood cuttings, and eye budding. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEIYEJOI'.

The first offer for sale of the new variety was Mar. 1, 2021 in the U.S. by the inventor or another who obtained the new variety directly or indirectly from the inventor.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately two years of age and were observed during September while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—observe.

Element 7—illustrates a specimen of an open flower—plan view—reverse.

Element 8—illustrates a specimen of a fully open flower—plan view—observe.

Element 9—illustrates a specimen of a fully open flower—plan view—reverse.

Element 10—illustrates a specimen of a floral receptacle showing arrangement of the pistils (stamens removed).

Element 11—illustrates a specimen of a floral receptacle showing arrangement of the stamens and pistils.

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

Element 19—illustrates a specimen of a leaf with 9 leaflets—plan view—upper surface.

Element 20—illustrates a specimen of a leaf with 9 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of two-years-old specimens of the new variety during September while budded on their own roots and growing outdoors at Le Cannet des Maures, Var, France.

Commercial classification: Miniature Rose Plant.

Plant:

*Habit*.—Bushy.

*Height*.—Typically 40 to 70 cm on average.

*Width*.—Typically 50 to 80 cm on average.

Branches:

*Color*.—Young stems: commonly near Green Group 143A. — adult wood: commonly near Yellow-Green Group 144A.

*Length*.—From the crown to the flower is approximately between 25 to 50 cm on average.

*Diameter*.—Approximately 0.3 cm on average.

*Young shoots*.—Anthocyanin coloration: absent.

*Thorns*.—Configuration on adult stems: elongated and slightly curved downwards on the upper surface and concave on the under surface. — long prickles — quantity: commonly approximately 4 to 7 thorns per 10 cm long young stem and commonly between 11 to 15 thorns per 10 cm long adult stem. — long prickles — base shape: narrow obovate. — long prickles — size: approximately between 0.7 to 1.0 cm in length on average on young stems and between 0.5 to 1.0 cm on average on adult stems. — long prickles — color: commonly near Yellow-Green Group 152C more or less covered with near Greyed-Orange Group 176A on young stems, and commonly near Greyed-Orange Group 165B with some flecks of near Greyed-Orange Group 166A on adult stems. — small prickles — quantity: absent.

*Internode*.—Numbers on the entire branch: approximately between 6 to 8 on average. — length: approximately between 1.5 to 3.5 cm on average.

Foliage:

*General appearance*.—Dense, dark with semi-glossy aspect.

*Number of leaflets*.—3, 5, 7, 9; most often 7.

*Terminal leaflet*.—Length: approximately between 1.5 to 3.0 cm on average. — width: approximately between 1.0 to 1.5 cm on average.

7 *leaflets leaf*.—Length: approximately between 7.0 and 9.0 cm on average. — width: approximately 5.0 cm on average.

*New foliage*.—Upper surface color: commonly near Green Group 143A. — under surface color: commonly near Green Group 143C. — anthocyanin coloration: absent.

*Adult foliage*.—Upper surface color: commonly near Green Group 139A. — under surface color: commonly near Green Group 138A. — anthocyanin coloration: absent.

Leaflets:

*Shape*.—Tip: acuminate. — base: obtuse.

*Glossiness of upper surface*.—Medium.

*Texture*.—Leathery.

*General appearance*.—Elliptical.

*Serration*.—Small and single.

*Undulation on the margin*.—Absent.

*Petiole rachis*.—Color of upper surface: commonly near Green Group 143A. — color of under surface: commonly near Green Group 143B. — texture: upper surface is smooth, under surface has few prickles. — rachis of terminal leaflet: length is between 2.5 and 3.5 cm on average, and width is approximately 0.1 cm on average.

*Petioles*.—Upper surface: no glandular. — under surface: very few prickles. — color of upper surface: commonly near Green Group 143B. — color of under surface: commonly near Green Group 143B. — length: approximately between 1.0 to 1.8 cm on average. — diameter: approximately near 0.1 cm on average

*Stipules*.—General appearance: adnate, pectinate and rather broad. — length: approximately between 0.5 to 1.0 cm on average. — width: approximately between 0.2 to 0.4 cm on average. — color of upper surface: commonly near Green Group 143B. — color of under surface: commonly near Green Group 141A.

Inflorescence:

*Number of flowers per stem*.—Typically 3 to 5 flowers per stem.

*Lastingness of the bloom*.—On the plant: approximately 15 days on average. — in vase: approximately 8 days on average.

*Bud*.—Shape: ovoid. — size: small. — length: approximately between 1.5 to 2.0 cm on average. — width: approximately between 1.5 to 2.0 cm on average. — color as calyx breaks: upper surface: commonly near Yellow Group 2D amply suffused with near Red-Purple Group 68C on the apical half, which evolves to Red-Purple Group 68A at the edge of the more external petals, basal spot commonly near Yellow Group 2B. under surface: commonly near Yellow Group 2D very slightly suffused with near Red-Purple Group 68C on the more external petals and less and less suffused near the internal petals.

*Sepals*.—Number: commonly 5. — length: approximately between 1.5 to 2.0 cm on average. — width: approximately between 0.4 to 0.5 cm on average. — shape: at the top: slightly elongated and narrow, at the base: broad. — extensions: commonly 3 sepals have medium to strong extensions and the other 2 sepals do not. — upper surface: texture: tomentous. color: commonly near Green Group 143B with a bit mixed up with near Green Group 141A and with some flecks of near Greyed-Purple Group 183A, everything is covered with silky fur of near White Group 155D. — under surface: texture: smooth. color: commonly near Green Group 143B with a bit mixed up with near Green Group 141A and with some flecks of near Greyed-Purple Group 183A.

*Receptacle*.—Color: commonly a mix between near Green Group 143B and Green Group 143C. — length: approximately between 0.4 to 0.6 cm on average. — width: approximately 0.6 to 0.7 cm on average. — surface: smooth. — shape: pyriform.

*Peduncle*.—Length: approximately 2.5 to 3.5 cm on average. — width: approximately 0.1 to 0.2 cm on average. — surface: smooth. — color: commonly near Yellow-Green Group 144A suffused sometimes with near Greyed-Purple Group 183A.

*Flower*.—Average size when open: approximately between 5.0 to 6.0 cm on average. — shape: flat cup shaped. — shape when viewed from above: irregularly round. — type: double. — number of petals under normal conditions: typically between 20 to 35 petals on average. — inner petals: shape: ovoid and narrow. texture: normal. length: approximately between 1.7 to 2.2 cm on average. width: approximately between 0.7 to 1.0 cm on average. — external petals: shape: longish and rounded. texture: firm. length: approximately between 2.2 to 2.3 cm on average. — width: approximately between 1.4 to 1.8 cm on average. — undulation of the petal: absent. — reflexing of the petal: weak. — petal incision: very weak. — petal arrangement: imbricated with some petaloids, which are the same shape as the petals. — petal drop: petals drop off cleanly before drying. — fragrance: none. — color when opening: little basal spot upper surface: commonly near Yellow Group 2B. upper surface of the flower: external petals are commonly near Yellow Group 2B suffused with a gradient color from Red-Purple Group 68D to 68A from the middle of the petals to the external edge; internal petals are near Yellow Group 2D suffused with near Red-Purple Group 68C on the apical half. little basal spot on under surface: commonly near Yellow Group 2B. under surface: commonly near Yellow Group 2D very slightly suffused with near Red-Purple Group 68C on the more external petals and less and less suffused near the internal petals. — color of the open flower: little basal spot on the upper surface: commonly near Yellow Group 2B. upper surface of the flower: commonly near Yellow Group 2D suffused on the apical half with near Red-Purple Group 68D and with near Red-Purple Group 68A on the external edge. little basal spot on the under surface: commonly near Yellow Group 2B. under surface of the flower: commonly near Yellow Group 2D very slightly suffused with near Red-Purple Group 68C on the apical half. — anthers: number is between 60 to 70 on average, length is approximately 0.1 cm on average, coloration is commonly near Yellow-Orange Group 22B, and arrangement is regular around styles. — filaments: length is approximately between 0.2 to 0.4 cm on average and coloration is commonly near Yellow Group 5A. — styles: length is approximately between 0.4 to 0.6 cm on average, coloration is commonly near Yellow Group 3D, and number is approximately between 30 to 40 on average. — stigmas: size is approximately 0.1 cm on average and coloration is commonly near Yellow Group 3D. — pollen: color is commonly near Yellow-Orange Group 17A and amount is medium to high. — hips: not available at this stage.

Development:

*Vegetation*.—Strong.

*Blooming*.—Early in the season and intermittent, typically from May to October in France.

*USDA hardiness zone*.—Zone 5.

*Tolerance to disease*.—Good, and particularly against rust (*Phragmidium* sp.) and powdery mildew (*Podosphaera pannosa*).

The new 'MEIYEJOI' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIYEJOI' characterized by the following combination of characteristics:

(a) is a very floriferous miniature variety, (b) forms a pink colored flower, and (c) exhibits a dark green, semi-glossy foliage; substantially as herein shown and described.

* * * * *

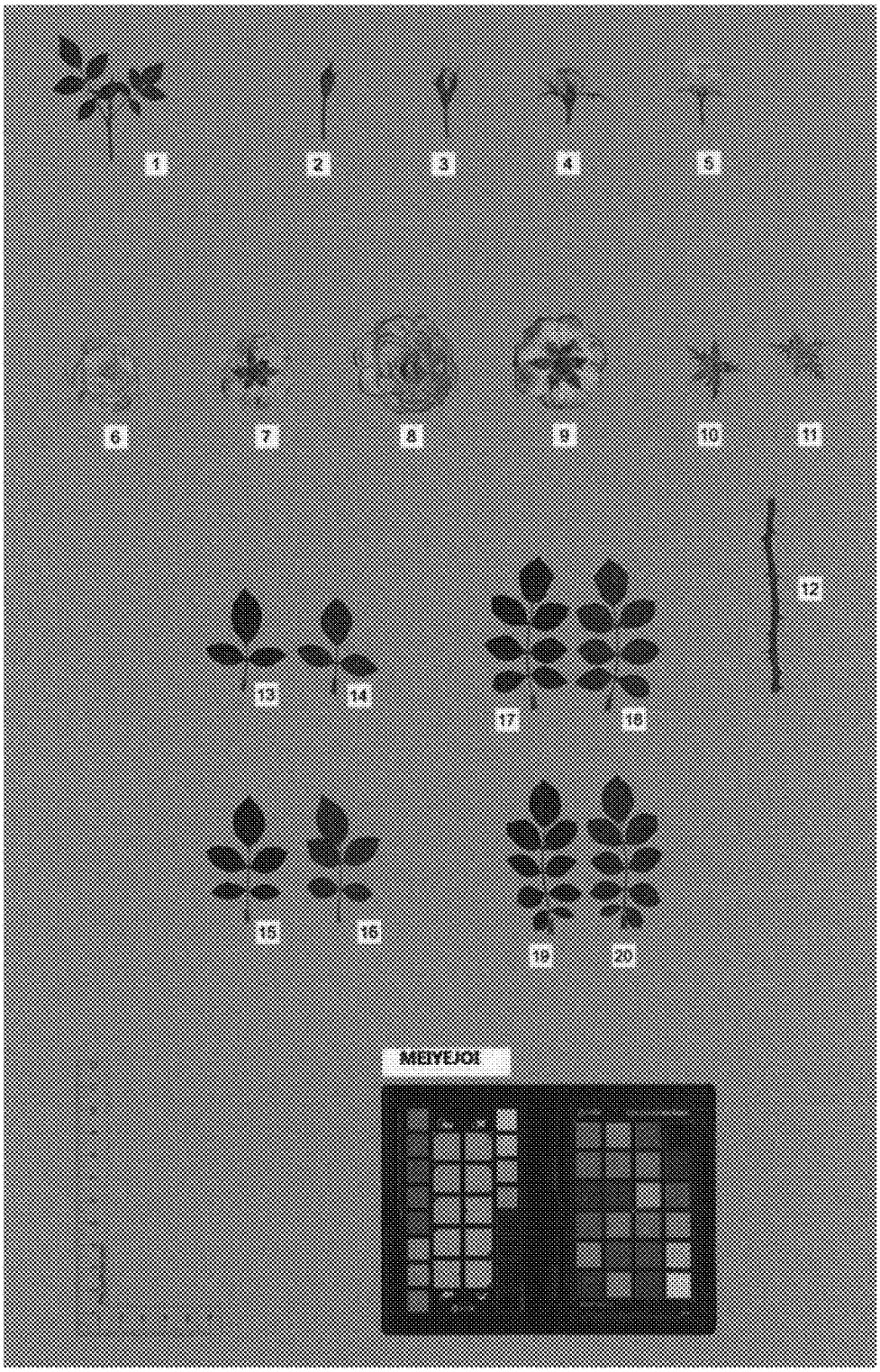
1
2
3
4
5
6
7
8
9
10
11
12
13
14
15
16
17
18
19
20
MEIYEJOI